United States Patent [19]
Tseng et al.

[11] Patent Number: 5,512,289
[45] Date of Patent: Apr. 30, 1996

[54] SPERMICIDAL ANTI-VIRAL LUBRICANT COMPOSITION AND METHOD OF USING SAME

[75] Inventors: Chung-Ye Tseng, Middletown; Jonas Wang, Robbinsville; Marilyn Hudson, Randolph; Jue-Chen Liu, Neshanic, all of N.J.

[73] Assignee: Johnson & Johnson Consumer Products, Inc., Skillman, N.J.

[21] Appl. No.: 495,737

[22] Filed: Jun. 8, 1995

Related U.S. Application Data

[63] Continuation of Ser. No. 98,588, Jul. 28, 1993, abandoned.

[51] Int. Cl.$^6$ .................... A61F 2/00; A61F 6/06
[52] U.S. Cl. .................... 424/426; 424/430; 424/486; 424/487; 424/488; 514/57; 514/568; 514/705; 514/731; 514/841; 514/843
[58] Field of Search .................... 424/422, 426, 424/430, 486, 487, 488, DIG. 14; 514/841, 843, 57, 568, 705, 731

[56] References Cited

U.S. PATENT DOCUMENTS

| | | | |
|---|---|---|---|
| 3,875,300 | 4/1975 | Homm et al. | 424/27 |
| 4,242,359 | 12/1980 | Cooper et al. | 424/325 |
| 4,317,447 | 3/1982 | Williams | 128/260 |
| 5,128,145 | 7/1992 | Edgren et al. | 424/439 |

*Primary Examiner*—Nathan M. Nutter

[57] ABSTRACT

A personal lubricant composition containing an antiviral, alkylphenoxypolyethoxyethanol spermicide, a water soluble polymer gel matrix and a solubilizer which permits the spermicide to be compatible with the gel matrix. Preferably, a polyethoxylated compound such as polyethoxylated castor oil may be used.

37 Claims, 1 Drawing Sheet

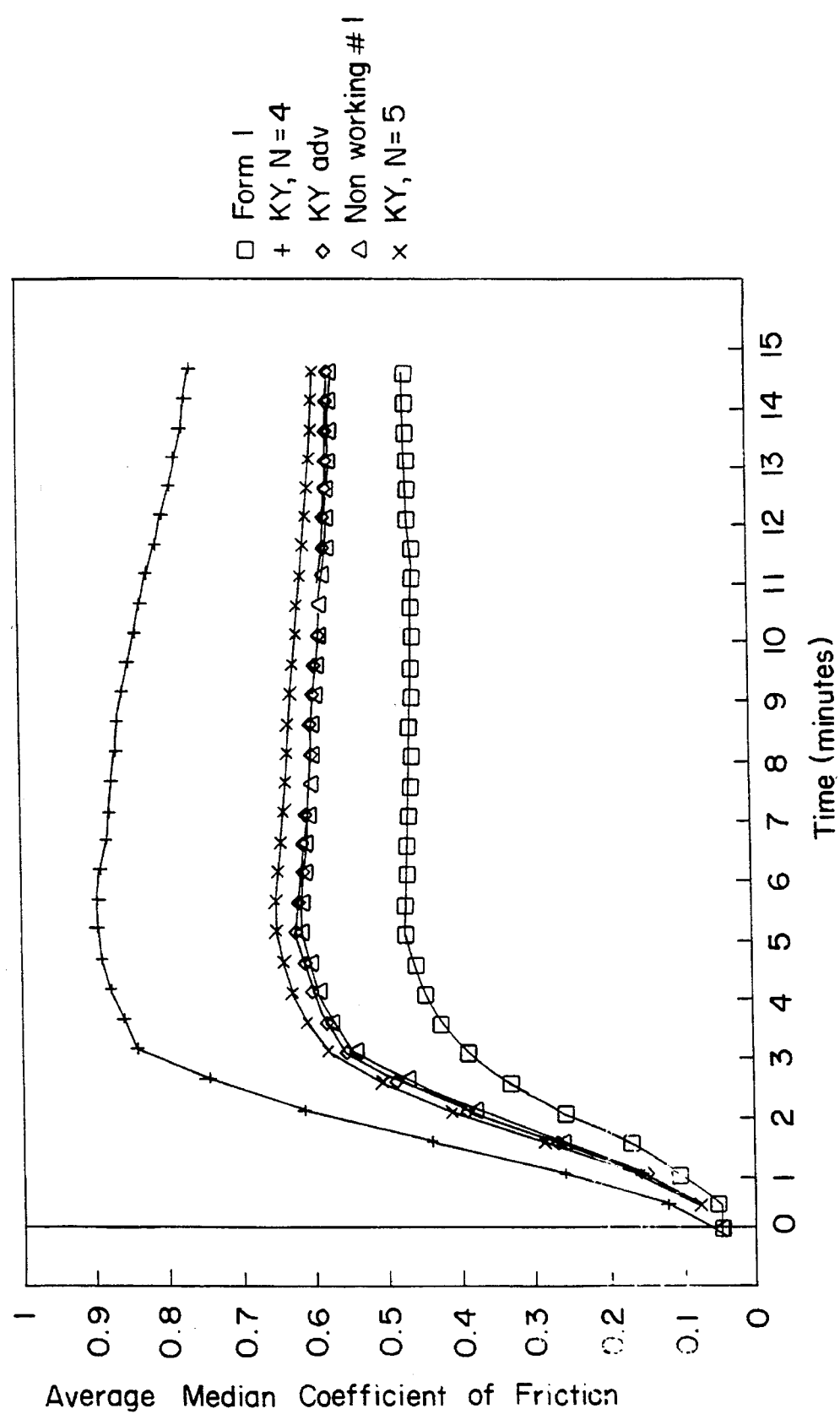

SPERMICIDAL ANTI-VIRAL LUBRICANT COMPOSITION AND METHOD OF USING SAME

This is a continuation of application Ser. No. 08/098/588, filed Jul. 28, 1993 and now abandoned.

BACKGROUND OF THE INVENTION

1. Field of the Invention

This invention relates to a lubricating composition containing a spermicidal/anti-viral component. More particularly, it relates to a spermicidal/anti-viral sexual lubricant composition which is stable and extremely lubricious.

2. Prior Art

For many years, women have used spermicidal products, such as nonoxynol-9, to prevent unwanted pregnancies. These products have been applied in formulations such as jellies, creams and foams. More recently, it has been found that nonoxynol-9 and its related spermicides can be effective in combatting sexually transmitted diseases caused by certain viruses, including Acquired Immune Deficiency Syndrome (AIDS). [See, for example, Stone et al., Am. J. Obstet. Gynecol., Vol. 155, p. 180 (1986); Voeller, Lancet, 1 (8490), 1153 (1986); and Louv et al., J. Infect. Dis., Vol. 158, 518 (1988)].

Although there are currently vaginal cream and jelly products intended for preventing pregnancies which are commercially available, the lubricating and spreading properties of these products are relatively poor. They can be grainy and are not capable of moisturizing the vagina, and, therefore, cause some discomfort in use. Furthermore, the main objective of these creams and jellies is to prevent pregnancy, rather than necessarily to function as a personal lubricant.

It has been suggested that anti-viral agents such as zinc or spermicides may be added to sexual lubricants in order to provides personal lubrication (European Patent Application 0 402 078, Kelly, published Dec. 12, 1990). However, the mere addition of a spermicide such as nonoxynol-9 to an existing polymer matrix can cause physical reactions which may destroy the polymer matrix and will not afford an effective personal lubricant.

Personal, or vaginal lubricants such as K-Y® brand lubricating Jelly, which contain hydroxyethylcellulose as a base, are known to afford vaginal moisturization and lubrication, as set forth in copending U.S. Pat. application Ser. No. 07/921,819. However, the addition of nonoxynol-9 or related spermicides to a hydroxyethylcellulose gel system tends to cause the hydroxyethylcellulose gel system to collapse.

It is, therefore, an object of this invention to provide a composition for lubricating and moisturizing the vagina and/or body cavities.

It is a further object of this invention to provide a spermicidal composition that has excellent moisturizing and lubricating properties.

Yet another object of this invention is to provide an antiviral composition that has good moisturizing and lubricating properties.

It is another object of this invention to provide a method of personal lubrication using the compositions of this invention.

Additional objects will become evident throughout the description of the compositions and methods set forth below.

SUMMARY OF THE INVENTION

This invention relates to a vaginal lubricant composition containing a water-soluble polymeric matrix, an alkylphenoxypolyethoxyethanol spermicide and a solubilizer in a pharmaceutically-acceptable carrier. More particularly, this invention relates to a vaginal lubricant composition containing a cellulose-derivative water-soluble polymeric matrix, a surfactant-type alkylphenoxypolyethoxyethanol spermicide and a solubilizer having the ability to permit the spermicide to be compatible with the water-soluble polymeric matrix.

The resulting gel composition is stable, clear, lubricious and spermicidally-efficacious. Furthermore, the stable gel composition of this invention maintains its pH in the range that is most compatible with the vagina, i.e., between 3 and 5.5.

BRIEF DESCRIPTION OF THE DRAWING

FIG. 1 is a graph depicting the coefficients of friction of several spermicide-containing compositions.

DETAILED DESCRIPTION OF THE PREFERRED EMBODIMENTS

The composition of this invention includes a spermicide, a water-soluble polymeric matrix and a solubilizing portion in a pharmaceutically-acceptable carrier.

The water-soluble polymeric gel matrix of the composition of this invention is, preferably, a lubricious compound or composition having an appropriate viscosity for adhesion to mucous membranes and a low coefficient of friction. It preferably has a viscosity between about 37,000 and about 150,000 centipoise (cPs). At this viscosity, the composition is capable of adhering to mucous membranes and thereby has a long-lasting effect. The viscosity may decrease over time. Its molecular weight should be greater than 700,000 and, more preferably, between about 900,000 and about 1,200,000. Higher molecular weight polymers will not have the appropriate high lubricity. Lower molecular weight polymers will not be stable in the presence of low-molecular weight spermicides.

The water-soluble polymer gel matrix of this composition is preferably a cellulose derivative. More preferably, the water-soluble polymer gel matrix of this composition is a hydroxyalkyl cellulose having a lower alkyl ($C_2$–$C_6$) moiety such as ethyl, propyl, butyl and the like. For example, hydroxypropyl methyl cellulose is useful in the compositions of this invention. Most preferably, hydroxyethyl cellulose is employed in the compositions of this invention. This water-soluble polymeric gel matrix is very lubricious and affords the lubricant composition a low viscosity and low coefficient of friction. Low viscosity and low coefficient of friction are desirable in personal lubricants in order to afford the user the expected lubricating properties of a personal lubricant.

The compounds that constitute the water-soluble polymer gel matrix of the compositions of this invention should be present in the composition in an amount between about 0.1 to about 10 weight per cent of the final composition. Most preferably, the water-soluble polymer gel matrix should be present in an amount between about 0.5 and about 3% by weight of the composition.

The water-soluble gel polymer matrix may, optionally, contain certain additional polymers such as polyvinyl pyrrolidone and carboxy-functional polymer. This polymer matrix is also capable of behaving as a bioadhesive polymeric system, providing and maintaining moisture in the vagina. The polyvinyl pyrrolidone has a molecular weight of about 10,000 to about 1,200,000. Carboxy-functional polymers suitable for use in a bioadhesive polymeric system include polyacrylic acid, carboxymethyl cellulose, and polymethylacrylic acid. These carboxy-functional polymers have a molecular weight of from about 90,000 to about 1,200,000. The composition may contain from about 0.1 to about 10%, preferably from about 0.2 to about 2%, by weight, of the polyvinyl pyrrolidone-carboxy functional polymer moiety. Most preferably, it should be about 0.45% by weight of the composition. The weight ratio of polyvinyl pyrrolidone to carboxy functional polymer is within the range of about 0.01:1 to about 5:1. When carboxymethyl cellulose is employed as the carboxy-functional polymer, the weight ratio of polyvinyl pyrrolidone to carboxymethyl cellulose is within the range of about 0.01:1 to about 4:1, preferably about 0.5:1 to about 2:1 and most preferably about 1:1.

To the water-soluble polymer gel matrix of the compositions of this invention are added spermicidal compounds. Preferred for use in the compositions of this invention are the alkylphenoxypolyethoxyethanol surfactant spermicides such as p-nonylphenoxypolyethoxyethanol (known as nonoxynol-9), p-octyl phenoxypolyethoxyethanol and the like, such as those described in U.S. Pat. No. 2,943,979.

In order to measure a compound's effectiveness as a spermicide, the "S-value" of the particular compound is measured. The "S-value" represents the number of dilutions a solution of the compound can be subjected to and still effect a 100% kill of the sperm in 0.2 ml of human semen in accordance with the Sander-Cramer Method (Sander, et al., J. Human Fertility, Vol. 6, p. 134 (1941)). Nonoxynol-9, for example, has a relatively high S-value. Preferably, the S-value of the spermicide employed in the compositions of this invention is 12 or greater. Preferably, nonoxynol-9 is utilized. The average molecular weight of the nonoxynol-9 should be about 630.

Another means of describing the properties of a surfactant such as the spermicidal surfactants employed in the compositions of this invention is the Hydrophile-Lipophile Balance, or "HLB". This measurement is based upon the observation that one portion of a surfactant molecule is lipophilic while the other portion of the molecule is hydrophilic. The weights of these two fractions are not necessarily equal and, when compared, provide the "HLB" number. Thus, the HLB number of a surfactant is calculated on the basis of the respective weight proportions of the hydrophilic and lipophilic moieties of the surfactant molecule. The HLB values of known surfactants is published in McCutcheon's Emulsifier & Detergents, Vol. 1, North American Ed., 1992. For example, the HLB value of nonoxynol-9 is 13.

The solubilizer moiety enables the water-soluble polymer matrix to maintain its integrity when exposed to the surfactant-type spermicides used in the compositions of this invention. The mere addition of spermicide to a water-soluble polymer matrix, such as hydroxyalkyl cellulose, tends to destroy the gel matrix and cause its collapse. Surprisingly, the addition of a solubilizer according to this invention substantially prevents the collapse of the gel matrix and permits the gel matrix to maintain its properties in the compositions of this invention.

Preferably, the solubilizer moiety should be a non-ionic compound having a hydrophile-lipophile balance (HLB) between about 10 and about 16. This permits the solubilizer moiety to be compatible with the surfactant-type spermicides used in the compositions of this invention. Nonoxynol-9, for example, has an HLB of about 13. Preferably, the solubilizer should be a polyethoxylated compound having a high ethylene oxide (EO) content. The ethylene oxide content is determined in accordance with ASTM Test No. D 4875-88. The EO content should be at least 20 moles. The molecular weight of the solubilizer moiety should be greater than of the spermicide moiety. Thus, the solubilizer moiety should have a molecular weight between about 600 and about 5,000. A solubilizer with molecular weight greater than about 5,000 would not be acceptable due to its disproportionate size with regard to the spermicide. Furthermore, its HLB would probably be excessively high to be compatible with the spermicide. The solubilizer should be relatively close in weight to that of the spermicide compound employed.

More preferably, the solubilizer moiety of the composition of this invention is an ethoxylated esters or ethers, or ethoxylated fatty acid derivatives wherein the fatty acid moiety contains between 8 and 16 carbon atoms. Thus, suitable solubilizers include polyethoxylated alkyl ethers, polyethylene glycol sorbitan fatty acid esters, polyethoxylated castor oils and the like. Most preferably, polyethoxylated, hydrogenated castor oils may be used to produce a clear, low-viscosity personal lubricant composition. The polyethoxylated castor oil may be hydrogenated or non-hydrogenated, however, the castor oil is most preferably hydrogenated.

The spermicidal compositions of this invention may be dispersed by use of a pharmaceutically acceptable vehicle. This vehicle must also be capable of being used in or on humans or other mammals without causing any ill effects, such as toxicity or severe irritation to the skin or mucosal tissue. Pharmaceutically acceptable vehicles suitable for use in the compositions of this invention include water, alcohols, such as ethanol, glycerine, and propylene glycol, and the like, and mixtures thereof. The dispersion preferably takes the form of a liquid suspension, such as a gel, employing water as a vehicle.

The composition of this invention contains a sufficient amount of the vehicle to form any of the aforementioned dispersions. The composition preferably contains from about 30 to about 95, more preferably from about 50 to about 85, weight percent of the vehicle, such as water.

The compositions of this invention should remain stable over time without separating into different constituent components. Preferably, the compositions should remain stable for twenty weeks at 30° C., 40° C. or 50° C. or at room temperature for one year.

The compositions of this invention are preferably made using the following method. First, a slurry should be made with an appropriate carrier material, preferably, propylene glycol or glycerine. If propylene glycol is used, it should be heated to a temperature of about 45° to about 57° C. Constituents such as preservatives should be added to the propylene glycol and mixed until the solution is clear. This slurry should then be set aside to cool to about room temperature. A premix constituting the spermicide and the solubilizer should then be made. The premix should be maintained at a temperature of between about 40° and 50° C. and mixed for about ten to about fifteen minutes. If polyethoxylated castor oil such as Cremophor is used, it should be premelted prior to mixing with the spermicide.

Preferably, water is used as a carrier. Preferably, the solubilizer/spermicide premix is added to the water carrier and mixed at about 500 rpm using a sweep agitator for about fifteen minutes. The water-soluble polymer gel matrix, such as hydroxyethyl cellulose, should then be added to the cooled slurry and mixed until it is dispersed (about fifteen minutes). The slurry should then be added to the solubilizer/ spermicide/water solution and mixed at about 500 rpm with a sweep agitator for about fifteen to about twenty minutes. If necessary, a pH adjustor such as sodium hydroxide may be added and then mixed at about 500 rpm for about ten to about fifteen minutes. Most preferably, the composition is then mixed at a lower speed, about 400 rpm for about three hours to result in an acceptable gel composition in accordance with this invention. It is important to mix the spermicide with the solubilizer prior to adding it to the remainder of the composition in order to ensure that the spermicide will be compatible with the water-soluble polymer gel matrix.

The pH of the compositions of this invention should be between about 3 and about 5.5 in order to be compatible with the vaginal mucosa. The water-soluble polymer matrix generally should have a pH of about 4.5. Hydroxyethyl cellulose, for example, has a pH of about 4.5. The spermicide might, without the solubilizer moiety of this invention, raise the pH of the composition by interfering or reacting with the polymer gel matrix so as to change the pH. Because the spermicide is solubilized in the compositions of this invention, and therefore substantially prevented from reacting with the polymer gel matrix, the hydroxyethyl cellulose is permitted to maintain the appropriate pH without the use of additional buffers.

When the composition of this invention is a personal lubricant in the form of a gel, it generally contains:
- about 0.5 to about 5 percent by weight hydroxyalkyl cellulose water-soluble polymer;
- about 0.5 to about 5 percent by weight alkylphenoxy polyethoxyethanol spermicide;
- about 0.5 to about 5 percent by weight ethoxylated solubilizer;
- about 10 to about 40 percent by weight propylene glycol or glycerine; and
- about 50 to about 85 percent by weight water, and has a pH of about 3 to about 5.5.

Most preferably, the composition of this invention is a clear lubricious gel having a viscosity of about 40,000 to about 150,000 centipoise and containing the following:
- about 10 to about 20 weight percent of propylene glycol;
- about 2 to about 3 weight percent hydroxyethylcellulose;
- about 2 to about 3 weight percent nonoxynol-9; and
- about 1.5 to about 3 weight percent polyethoxylated castor oil.

Preferably, the ratio of spermicide to solubilizer is about 5:1 to about 0.5:1. More preferably, the ratio of spermicide to solubilizer is about 1.1:1. Preferably, the ratio of spermicide to water-soluble polymer matrix is about 5:1 to about 0.5:1. More preferably, the ratio of spermicide to water-soluble polymer matrix is about 1:1. Preferably, the ratio of solubilizer to water-soluble polymer matrix is from about 0.5:2 to about 1:1. More preferably, the ratio of solubilizer to water-soluble polymer matrix is about 0.87:1.

It is believed that too small a proportion of solubilizer with respect to spermicide will tend to turn the gel hazy and somewhat incompatible, while too much solubilizer with respect to spermicide will make the viscosity of the gel decrease, as the solubilizer has an affinity for water and tends to cause the gel to collapse.

It is theorized that too small a proportion of water-soluble polymer matrix with respect to the solubilizer in the composition will result in a composition that will not gel and will have low viscosity. Too much polymer matrix in the compsosition will result in a very stiff, not very lubricious gel. If too much water-soluble polymer is added with respect to the spermicide, it is theorized that the two components will tend to compete with the spermicide for water in the gel and will result in a rigid, unstable gel. Too small an amount of polymer with respect to the amount of spermicide will likely result in a polymer that will not form a gel, rather, will form a thick liquid.

Suitable personal lubricants may include hydroxyethyl cellulose, glycerine, mineral oil, petrolatum, silicones, lanolin, lanolin oil, polyethylene glycol and triglycerides. The composition may also contain buffering agents to assist in maintaining the pH of the formulation such as sorbic acid, citric acid and sodium hydroxide and preservatives such as chlorhexidene gluconate (CHG).

Antiviral/spermicidal agents suitable for use in the compositions of this invention include nonoxynol-9, octoxynol-9 and menfegol, dodecaethylene glycol monolaurate, Laureth IOS, and methoxypropyloxyethylene glycol laurate-550.

Deodorants and fragrances useful in the compositions of this invention include sodium bicarbonate, aluminum chloride, aluminum chlorohydrates, aluminum zirconium chlorohydrates, buffered aluminum sulfate, triclosan and triclhorocarbanilide.

The compositions of this invention may also contain pharmaceutically or cosmetically acceptable additives. These additives include stabilizers, preservatives, excipients, binders, vehicles, chelating agents, antioxidants, coloring agents, flavors, odor controlling agents and the like.

The compositions of this invention may be used by individuals for personal lubrication when antiviral, spermicidal activity is desired. for example, the compositions may be applied to the body externally or internally. The compositions may be applied to the abody externally or internally. The compositions may be applied digitally or with an applicator, or may be applied to a condom or a diaphragm.

EXAMPLE 1

A personal lubricant gel of this invention was prepared having the formulation shown in Table 1.

TABLE 1

| Ingredient | Formulation 1 (% by Weight) |
| --- | --- |
| Water | 76.08 |
| Propylene Glycol | 17.00 |
| Hydroxyethyl cellulose (Natrosol) | 2.30 |
| Nonoxynol-9 | 2.20 |
| Polyethoxylated castor oil | 2.00 |
| Methylparaben | 0.20 |
| Sorbic Acid | 0.20 |
| Sodium Hydroxide | 0.02 |

This gel was prepared by premixing at 50° C. Igepal CO630SP nonoxynol-9 commercially available from Phone-Poulenc Company of Monmouth Junction, N.J., and hydrogenated polyethoxylated castor oil, which is commercially available from BASF Corporation as Cremophor RH-60. In a separate beaker was measured 35 grams of propylene glycol to which was added methylparaben and sorbic acid. This solution was heated to 80° C. using a stir bar until the solution was clear. This solution was added to the water in a separate beaker. The pH of this solution was 3.59, which was adjusted with 1.5 grams of sodium hydroxide (sol. at 10%). In a separate beaker, 50 grams of proylene glycol were measured, to which was added Natrosol brand hydroxyethyl cellulose, commercially available from Aqualon Company, Wilmington, Del.). This solution was mixed at high speed until dispersed and then added to the water solution. The solution was then mixed on medium speed for three hours. The resulting gel had a viscosity of 110,000 centipoise (cPs)(Brookfield RVT, #27, 1 rpm, 3 min.) and a pH of 4.8. The spermicide and the hydroxyethyl cellulose gel from matrix were compatible and the composition was clear.

EXAMPLES 2 AND 3

The gel compositions of this invention described in Table 2, below, were made using the method set forth in Example 1 except for certain steps noted below. Each resulted in a compatible, clear gel, having acceptable viscosity and pH.

Formulation 2 was made by adding the polyvinyl prryolidone to water, then adding citric acid. The spermicide/ solubilizer premix was then added to the PVP and citric acid solution. Carboxymethyl cellulose was then sprinkled into the solution and the solution mixed. A separate slurry was made by heating one-half of the glycerine, adding sorbic acid and methylparaben. One-half the glycerine solution was added to hydroxyethylcellulose and the solution stirred to form a slurry. The slurry was then combined with the premix and processed in accordance with Example 1.

Formulation 3 was made by adding CHG and a buffer to water and adjusting the pH. PVP was then added directly to the water. The premix of Cremaphor and Nonoxynol-9 was then added to the water. A slurry of glycerine and Natrosol was made. The solutions were then combined.

TABLE 2

| Ingredient | (% by Weight) |
|---|---|
| Formulation 2 | |
| Water | 75.50 |
| Glycerine | 17.00 |
| Hydroxyethyl cellulose | 1.00 |
| Polyvinyl pyrrolidone | 0.90 |
| Carboxymethyl cellulose | 1.00 |
| Nonoxynol-9 | 2.00 |
| Polyethoxylated castor oil | 2.00 |
| Methylparaben | 0.20 |
| Sorbic Acid | 0.05 |
| Citric Acid | 0.35 |
| Formulation 3 | |
| Water | 75.66 |
| Glycerine | 17.00 |
| Hydroxyethyl cellulose | 2.30 |
| Nonoxynol-9 | 2.00 |
| Polyethoxylated castor oil | 2.00 |
| Glucono lactone | 0.50 |
| CHG (18.9% solution) | 0.25 |
| Methylparaben | 0.20 |
| Sodium hydroxide | 0.09 |

EXAMPLE 4: NON-WORKING EXAMPLES

Direct addition of nonoxynol-9 to a formulation containing hydroxyethyl cellulose, e.g., K-Y® Jelly brand personal lubricant available from Johnson & Johnson Consumer Products, Inc. in Skillman, N.J., resulted in an unstable, hazy gel product which was not acceptable for use as a spermicidal personal lubricant.

| NON-WORKING FORMULATION 1 | |
|---|---|
| Water | 77.50 |
| Glycerine | 17.00 |
| Hydroxyethyl cellulose | 1.00 |
| PVP | 0.90 |
| CMC | 1.00 |
| Nonoxynol-9 | 2.00 |
| Methylparaben | 0.20 |
| Sorbic Acid | 0.05 |
| Citric Acid | 0.35 |

Non-working Formulation 1 was made by heating glycerine, dissolving the preservatives in the glycerine, sprinkling in CMC, PVP and adding the Natrosol. The citric acid was then added to a separate water solution. The Nonoxynol-9 was then added to the water solution. The glycerine slurry was then added to the water solution and the composition mixed.

| NON-WORKING FORMULATION 2 | |
|---|---|
| Water | 78.50 |
| Glycerine | 17.00 |
| Hydroxyethyl cellulose | 1.00 |
| PVP | 0.90 |
| CMC | 1.00 |
| Nonoxynol-9 | 1.00 |
| Methylparaben | 0.20 |
| Sorbic Acid | 0.05 |
| Citric Acid | 0.35 |

Non-working formulation 2 was made in the same manner as set forth above for non-working Formulation 1.

| NON-WORKING FORMULATION 3 | |
|---|---|
| Water | 77.40 |
| Glycerine | 17.00 |
| Hydroxyethyl cellulose | 1.00 |
| CMC | 1.00 |
| Nonoxynol-9 | 2.00 |
| Methylparaben | 0.20 |
| Sorbic Acid | 0.05 |
| Citric Acid | 0.35 |
| Tween 80 | 1.00 |

Non-working Formulation 3 was made by forming a glycerine slurry with glycerine, sorbic acid, citric acid and HEC. The Tween 80 was then added to the water, after which the nonoxynol-9 was added to the water and the solutions combined. This Formulation resulted in syneresis.

| NON-WORKING FORMULATION 5 | |
|---|---|
| Water | 77.66 |
| Glycerine | 17.00 |
| Hydroxyethylcellulose | 2.30 |
| Nonoxynol-9 | 2.00 |
| Glucono lactone | 0.50 |
| CHG | 0.25 |
| Methylparaben | 0.20 |
| Sodium Hydroxide | 0.90 |

Non-working Formulation 5 was made in accordance with the method for making Non-working Formulation 1, above.

Non-working Formulations 1–7 resulted in compositions that were not compatible. The components physically separated, resulting in syneresis. These formulations were unstable upon aging at 30°, 40° and 50° C. None of these formulations contained a solubilizer component. Direct addition of nonoxynol-9 to a three-component gel system containing PVP, CMC and HEC, as set forth in Non-working formulations 1, 2, 3, 4 and 5 resulted in a physically unstable hazy and lumpy gel.

EXAMPLES 5–7 - FORMULATIONS 5–7

The following Formulations 5–7 were made using polyethoxylated sorbitans such as Tween 20 and Tween 80, commercially available from ICI Americas, Specialty Chemicals, of Wilmington, Del., as the solubilizer. In Formulation 5, Tego L5351, a cocamidopropyl betaine viscosity stabilizer available from the Goldschmidt Chemical Corporation of Virginia was used as the solubilizer. It should be noted that certain polyethoxylated sorbitans, such as Tween 20 and other solubilizers, may tend to inactivate the spermicidal activity of the nonoxynol-9. The following formulations were made using the method set forth in Example 1. They resulted in compatible gels that were somewhat hazy in appearance, but that possessed acceptable pH and viscosity for use in the compositions of this invention.

| FORMULATION 5 | |
| --- | --- |
| Water | 76.50 |
| Glycerine | 17.00 |
| Natrosol hydroxyethylcellulose | 1.00 |
| PVP | 0.90 |
| CMC | 1.00 |
| Nonoxynol-9 | 2.00 |
| Methylparaben | 0.20 |
| Sorbic Acid | 0.05 |
| Citric Acid | 0.35 |
| Tego Betaine L5351 | 1.00 |

This Formulation was made by heating the glycerine and dissolving the preservatives therein. The slurry was then cooled. The CMC was then sprinkled into the water, PVP and Natrosol were then added to the water. Citric acid was added separately to water, Tego Betaine was then added to the water. The nonoxynol-9 was then added to the water, after which the slurry was mixed with the water solution.

| FORMULATION 6 | |
| --- | --- |
| Water | 76.00 |
| Glycerine | 17.00 |
| Natrosol hydroxyethylcellulose | 0.50 |
| PVP | 0.90 |
| CMC | 1.00 |
| Nonoxynol-9 | 2.00 |
| Methylparaben | 0.20 |
| Sorbic Acid | 0.05 |
| Citric Acid | 0.35 |
| Tween 20 polyethoxylated sorbitan | 1.00 |

A preblend of nonoxynol-9 and Tween 20 was made. PVP was separately added to water, then pH was adjusted with citric acid. The preblend was added to the water solution. After this, the CMC was added. One-half the glycerine was separately mixed with the preservatives and added to the water solution. The remainder of the glycerine was slurried with HEC and combined with the water solution.

| FORMULATION 7 | |
| --- | --- |
| Water | 77.50 |
| Glycerine | 17.00 |
| PVP | 0.90 |
| CMC | 1.00 |
| Nonoxynol-9 | 2.00 |
| Methylparaben | 0.20 |
| Sorbic Acid | 0.05 |
| Citric Acid | 0.35 |
| Tween 80 polyethoxylated sorbitan | 1.00 |

Formulation 7 may be made in the same manner as that of Formulation 6. It appears that the addition of PVP to the water solution prior to the addition of the nonoxynol-9 might improve the compatibility of the nonoxynol-9 in the compositions of this invention.

EXAMPLE 11

A test was conducted to measure the lubricity of the personal lubricants of this invention, and several prior art personal lubricants which are commercially available. The coefficient of friction of each test sample was measured over time in an environment maintained at 80% relative humidity.

The tests were conducted on a custom-made friction testing apparatus. The apparatus contained a probe which was moved over a fixed base. The probe was in the form of a spring biased wheel mounted about an axle. The axle was supported by a moveable platform which was disposed over the fixed base. The test sample was interposed between the wheel and the base, and the platform was moved parallel to the base while the wheel exerted a known amount of normal (or downward) force on the test sample and base. Based on the amount of wheel rotation, a computer was used to calculate the coefficient of friction of the test sample.

In order to more closely simulate the conditions under which a personal lubricant is used, a NU-GEL® hydrogel pad was secured to the base. The hydrogel pad was then covered with a natural membrane condom made from sheep caecum. A small block of styrofoam (85 mm long, 25 mm wide and 12 mm thick was secured to the wheel in such a way that the frictional forces sensed by the styrofoam block were transmitted proportionally to the wheel, so that the coefficient of friction could be measured. The styrofoam was also covered with a sheep caecum membrane. The membranes were rinsed with water and kept moist by applying wet paper towels. The excess water was removed prior to testing by blotting with a paper towel.

The test sample (2 cc) was spread uniformly over the bottom of the block of styrofoam. The block/probe assembly was then placed on the base and the coefficient of friction was measured over a 15 minute period.

The coefficients of friction of current KY® Jelly (containing 79.86% water, 17% glycerine, 2.30% Natrosol 250H, 0.50% gluco lactone, 0.05% CHG, 0.09% sodium hydroxide and 0.20% methyl paraben), KY-Advance® (containing 79.00% water, 17.00% glycerine, 1.50% Natrosol 250H, 1.00% CMC, 0.90% PVP, 0.20% methyl paraben, 0.05% sorbic acid and 0.35% citric acid), the Non-working Formulation 1 of Example 6 and the personal lubricant of Formulation 1 set forth in Example 1 were measured. The results of this test are illustrated in FIG. 1, which shows the Average Median Coefficient of Friction plotted against time in minutes. The results show that the product of Formulation 1 has the lowest coefficient of friction of the tested products. It should be noted that the date in FIG. 1 denoted "KY Current" was taken from a trial conducted on a sample that had been heated and was not fresh.

EXAMPLE 12

The viscosity of various personal lubricant compositions was measured using a Haake Rotovisco™ device in accordance with the method set forth in Henderson, et al, Journal of Pharmaceutical Science, Vol. 50, p. 788 (1961). The viscosities were measured at varying shear rates. All tests were run at 25° C. Composition A was Regular KY® Jelly, commercially available from Johnson & Johnson Consumer Products, Inc., Skillman, N.J., lot #3402L, having the formulation set forth in Example 12; Composition B was the composition of Formulation 1; Composition C was Gynol II® spermicidal jelly commercially available from Ortho Advanced Care Products of Raritan, N.J., lot #22C100A, containing nonoxynol-9 (2%), lactic acid, methylparaben, povidone, propylene glycol, water, sodium carboxymethylcellulose, sorbic acid, and sorbitol solution; and Composition D was Ramses® Clear Gel product, commercially available from Schmid Laboratories, Sarasota, Fla., lot #L022-21, containing nonoxynol-9 (5%), 5% ethyl alcohol, boric acid, butylparaben, cellulose gums, fragrance, glycerine and water. The results of this example are set forth in Table 5.

TABLE 5

| Com- position | Absolute Viscosity (cps) (D[sec$^{-1}$])* | | | | |
|---|---|---|---|---|---|
| | D = 2.0 | D = 10.0 | D = 20.0 | D = 30.0 | D = 100.0 |
| A | 53,140 | 17,330 | 10,200 | 7,390 | 1,027 |
| B | 47,600 | 17,220 | 9,793 | 7,047 | 2,732 |
| C | 132,900 | 39,840 | 22,180 | 16,290 | 6,507 |
| D | 118,300 | 38,120 | 23,310 | 17,210 | 7,335 |

*D[sec$^{-1}$] represents shear rate, estimates from Henderson et al.: squeezing a lotion from a plastic bottle = 5 to 10; applying a hand lotion = 10 to 20; buttering bread = 10 to 50; topical application = 120.

Thus, the viscosities of Formulation 1 (composition B) are considerably lower than those of commercially available spermicidal jellies, and more consistent with those of KY® Jelly, a commercially available personal lubricant that does not contain a spermicide. The viscosities remained within the acceptable range for the purposes of personal lubrication. Surprisingly, this was achieved with the composition of this invention, indicating that the compositions of this invention have the desired viscosity in a stable, spermicide-containing formulation.

The foregoing examples are intended to be illustrative of the present invention. Various changes and modifications can be made to the above-described embodiments without departing from the spirit and scope of the present invention.

What is claimed is:

1. A composition, comprising:
   a water-soluble polymeric gel matrix comprising a hydroxyalkyl cellulose, wherein said alkyl moiety has from 2 to 6 carbon atoms;
   an alkylphenoxypolyethoxyethanol spermicide; and
   a solubilizing moiety comprising a polyethoxylated non-ionic compound.

2. A composition according to claim 1 wherein said water-soluble polymeric matrix comprises a hydroxyalkyl cellulose, wherein said alkyl moiety has from 2 to 6 carbon atoms.

3. A composition according to claim 1 wherein said alkylphenoxypolyethanol spermicide is selected from the group consisting of p-nonylphenoxy polyethoxy ethanol and p-octyl phenoxy polyethoxyethanol.

4. A composition according to claim 1 wherein said solubilizing moiety comprises a polyethoxylated non-ionic compounds having a hydrophile-lipophile balance between about 10 and about 16.

5. A composition according to claim 3 wherein said alkylphenoxypolyethanol spermicide is p-nonylphenoxy polyethoxy ethanol.

6. A composition according to claim 2 wherein said water-soluble polymer matrix comprises hydroxyethylcellulose.

7. A composition according to claim 1 wherein said water-soluble polymer matrix comprises a hydroxyalkyl cellulose, wherein said alkyl moiety has between 2 and 6 carbon atoms and polyvinyl pyrrolidone.

8. A composition according to claim 1 wherein said water-soluble polymer matrix comprises a hydroxyalkyl cellulose, wherein said alkyl moiety has between 2 and 6 carbon atoms and a carboxy-functional polymer.

9. A composition according to claim 8 wherein said carboxy-functional polymer is carboxy-methyl cellulose.

10. A composition according to claim 4 wherein said polyethoxylated non-ionic compound is selected from the group consisting of ethoxylated esters, ethers and ethoxylated fatty acid derivatives.

11. A composition according to claim 10 wherein said polyethoxylated non-ionic compound is a polyethoxylated alkyl ether.

12. A composition according to claim 10 wherein said polyethoxylated non-ionic compound is a polyethylene glycol sorbitan fatty acid ester.

13. A composition according to claim 10 wherein said polyethoxylated non-ionic compound is a polyethoxylated castor oil.

14. A composition according to claim 13 wherein said polyethoxylated castor oil is hydrogenated.

15. A composition according to claim 1 wherein said polyethoxylated solubilizer has an EO content of at least 20 moles.

16. A composition according to claim 1 wherein said polyethoxylated solubilizer compound has a molecular weight of between about 600 and about 5,000.

17. A personal lubricant composition, comprising:
   a water-soluble polymeric matrix comprising a cellulose derivative;
   an alkylphenoxypolyethoxyethanol spermicide; and
   a solubilizing moiety comprising a polyethoxylated non-ionic compound.

18. A personal lubricant composition according to claim 17 wherein said water-soluble polymeric matrix comprises a hydroxyalkyl cellulose, wherein said alkyl moiety has between 2 and 6 carbon atoms.

19. A personal lubricant composition according to claim 17 wherein said alkylphenoxypolyethanol spermicide is selected from the group consisting of p-nonylphenoxy polyethoxy ethanol and p-octyl phenoxy polyethoxyethanol.

20. A personal lubricant composition according to claim 17 wherein said solubilizing moiety comprises a polyethoxylated non-ionic compounds having a hydrophilelipophile balance between about 10 and about 16.

21. A personal lubricant composition according to claim 19 wherein said alkylphenoxypolyethanol spermicide is p-nonylphenoxy polyethoxy ethanol.

22. A personal lubricant composition according to claim 18 wherein said water-soluble polymer matrix comprises hydroxyethylcellulose.

23. A personal lubricant composition according to claim 17 wherein said water-soluble polymer matrix comprises a hydroxyalkyl cellulose, wherein said alkyl moiety has between 2 and 6 carbon atoms and polyvinyl pyrrolidone.

24. A personal lubricant composition according to claim 17 wherein said water-soluble polymer matrix comprises a hydroxyalkyl cellulose, wherein said alkyl moiety has between 2 and 6 carbon atoms and a carboxy-functional polymer.

25. A personal lubricant composition according to claim 24 wherein said carboxy-functional polymer is carboxymethyl cellulose.

26. A personal lubricant composition according to claim 20 wherein said polyethoxylated non-ionic compound is selected from the group consisting of ethoxylated esters, ethers and ethoxylated fatty acid derivatives.

27. A personal lubricant composition according to claim 26 wherein said polyethoxylated non-ionic compound is a polyethoxylated alkyl ether.

28. A personal lubricant composition according to claim 26 wherein said polyethoxylated non-ionic compound is a polyethylene glycol sorbitan fatty acid ester.

29. A personal lubricant composition according to claim 26 wherein said polyethoxylated non-ionic compound is a polyethoxylated castor oil.

30. A personal lubricant composition according to claim 29 wherein said polyethoxylated castor oil is hydrogenated.

31. A personal lubricant composition according to claim 17 wherein said polyethoxylated solubilizer has an EO content of at least 20 moles.

32. A personal lubricant composition according to claim 17 wherein said polyethoxylated solubilizer compound has a molecular weight of between about 600 and about 5,000.

33. A composition according to claim 1 wherein said composition has a viscosity between about 35,000 and about 120,000.

34. A composition according to claim 1 wherein the ratio of spermicide to solubilizer is about 5:1 to about 0.5:1.

35. A composition according to claim 1 wherein the ratio of spermicide to water soluble polymer gel matrix is about 5:1 to about 0.5:1.

36. A composition according to claim 1 wherein the ratio of solubilizer to water soluble polymer gel matrix is about 0.8:1.

37. A method of combatting viruses comprising exposing said viruses to a composition comprising:

a water soluble polymeric matrix comprising a hydroxyalkyl cellulose, wherein said alkyl moiety has 2 to 6 carbon atoms;

an alkylphenoxypolyethoxyethanol spermicide; and a solubilizing moiety comprising a polyethoxylated non-ionic compound by using it as a personal lubricant.

* * * * *